United States Patent

Hamuro et al.

[11] Patent Number: 5,177,841
[45] Date of Patent: Jan. 12, 1993

[54] METHOD OF MANUFACTURING CERAMIC LAYERED PRODUCT

[75] Inventors: Mitsuro Hamuro; Kazuhiko Kubota, both of Kyoto, Japan

[73] Assignee: Murata Manufacturing Co., Ltd., Japan

[21] Appl. No.: 723,412

[22] Filed: Jul. 1, 1991

[30] Foreign Application Priority Data

Jul. 13, 1990 [JP] Japan .................................. 2-186502

[51] Int. Cl.$^5$ .............................................. H01G 4/00
[52] U.S. Cl. .................................. 29/25.42; 242/56.1; 264/61
[58] Field of Search ................... 29/25.42; 264/61, 64; 242/56.1

[56] References Cited

U.S. PATENT DOCUMENTS 3,456,313  7/1969  Rodriguez et al. ................. 29/25.42
3,597,816  8/1971  Zelenz .................................. 29/25.42

Primary Examiner—Carl E. Hall
Attorney, Agent, or Firm—Ostrolenk, Faber, Gerb & Soffen

[57] ABSTRACT

In order to manufacture a ceramic layered product for manufacturing a multilayer ceramic capacitor, a plurality of reels (23) are prepared, which are wound with a plurality of types of elongated mother ceramic sheets (12), each having a plurality of electrode patterns (14) and a plurality of registration marks (15) distributed along its longitudinal direction. The mother ceramic sheets (12) are drawn out from the respective reels (23) onto related sheet cutting stages (25). Regions including the electrode patterns (14) are punched from respective ones of the mother ceramic sheets (12) provided on a selected sheet cutting stage (25) by a cutting head (52) whose periphery is enclosed with a cutting edge (51) on the basis of the registration marks (15). Then the ceramic sheets (35) punched out from the mother sheet by the cutting head (52) are carried to a stacking jig (34) by the cutting head (52) and stacked with each other on the stacking jig (34).

11 Claims, 6 Drawing Sheets

METHOD OF MANUFACTURING CERAMIC LAYERED PRODUCT

BACKGROUND OF THE INVENTION

1. Field of the Invention

The present invention relates to a method of and an apparatus for manufacturing a ceramic layered product.

2. Description of the Background Art

In order to manufacture a multilayer ceramic electronic component such as a multilayer ceramic capacitor, a multilayer inductor or a multilayer circuit board, for example, raw ceramic sheets are stacked with each other to prepare a ceramic layered product. For example, a ceramic layered product for a multilayer ceramic capacitor has generally been obtained by the following method or apparatus:

As shown in FIG. 10, a previously prepared mother ceramic sheet is drawn out from a sheet drawing station 1 to an electrode printing/cutting station 2, where the mother ceramic sheet is punched while electrodes are simultaneously printed on the ceramic sheets, which are punched out from the mother ceramic sheet. After the punching step, the mother ceramic sheet is discharged as a scrap sheet, while the ceramic sheets provided with the electrodes are dried in a drying station 3, and thereafter stored in a sheet storage station 4.

The stored ceramic sheets are selected to provide the characteristics, such as capacitance, required for the multilayer ceramic capacitor to be obtained. They are stacked and aligned with each other on the basis of their end surfaces. Then the aligned ceramic sheets are inserted in a stacking jig, and subjected to press working.

However, the aforementioned system has the following problems:

(1) A large space is required in order to store the punched ceramic sheets.

(2) Since the electrodes are printed simultaneously with the cutting of the ceramic sheets through a mechanical positioning mechanism, electrode positions are not much dispersed in the same type of electrode patterns. When the electrode patterns are exchanged, however, the electrode positions are apt to be dispersed between the different types of electrode patterns.

(3) When the electrode patterns are exchanged, it takes much time to locate the electrode patterns on cutting positions.

(4) Since the ceramic sheets are aligned with each other on the basis of their end surfaces, the electrode positions of the aligned ceramic sheets still remain dispersed resulting from the problem described above in paragraph (2), to cause dispersion the capacitances of the multilayer ceramic capacitors obtained by this method. Further, the electrode positions may also be dispersed by the aligning operation itself.

(5) If static electricity is generated between the ceramic sheets, or if the ceramic sheets have small thicknesses, it is difficult to align the ceramic sheets.

(6) The aligned ceramic sheets may be displaced from each other when they are inserted in the stacking jig.

Due to such problems of the system shown in FIG. 10, it has been difficult to stack the ceramic sheets with high accuracy.

In order to solve the problems in relation to handling the ceramic sheets in the aforementioned system, the applicant has proposed the following system, which is not yet known in the art:

As shown in FIG. 11, a sheet drawing station 5 is continuously coupled through an electrode printing station 6, a drying station 7 and a cutting/stacking station 8 to a scrap sheet winding station 9. A ceramic layered product is taken out from the cutting/stacking station 8. The feature of this system resides in that the electrode printing station 6 and the drying station 7 are provided in front of the cutting/stacking station 8.

However, the aforementioned system has the following problems:

(1) This system can merely manufacture the same type of ceramic layered products in relation to electrode patterns.

(2) When the items are switched, it takes much time for setup operations such as exchange of print patterns, exchange of sheets and the like.

(3) The system requires leader and end sheets extending beyond the length of the apparatus or the production line, to cause reduction of the material yield.

(4) Due to the continuous steps, complicated operations are required for dealing with possible defective prints and returning to the normal operation.

(5) In order to obtain a ceramic layered product for a multilayer ceramic capacitor, in particular, it is necessary to frequently drive and stop a printer in order to continuously obtain both ceramic sheets provided with electrodes and those provided with no such electrodes. Thus, printing accuracy is deteriorated due to irregular printing conditions.

(6) This system is unsuitable for multi-item dab production because of the problems mentioned above in paragraphs (1) to (3), although the same is suitable for mass production with small setup changes.

SUMMARY OF THE INVENTION

Accordingly, an object of the present invention is to provide a method of and an apparatus for manufacturing a ceramic layered product, which can stack ceramic sheets with high accuracy and advantageously be used in multi-item dab production.

The inventive method of manufacturing a ceramic layered product comprises the steps of:

preparing a plurality of reels wound with a plurality of types of elongated mother ceramic sheets each having a plurality of electrode patterns, and a plurality of registration marks having constant positional relations to the electrode patterns, distributed along its longitudinal direction, drawing out the mother ceramic sheets from the plurality of reels onto related sheet cutting stages, punching a region including at least one of the electrode patterns from one of the mother ceramic sheets, on a selected one of the sheet cutting stages, on the basis of the registration marks, employing a cutting head whose periphery is enclosed with a cutting edge, and carrying the ceramic sheets, which have been punched out from the mother ceramic sheet by the cutting head, to a stacking jig, the ceramic sheets being carried by the cutting head, and stacking the ceramic sheets on the stacking jig.

The inventive apparatus for manufacturing a ceramic layered product comprises:

a reel stand for setting holding a plurality of reels wound with a plurality of types of mother ceramic sheets each having a plurality of electrode patterns, and a plurality of registration marks having constant positional relations to the electrode patterns, distributed along its longitudinal direction, the reels being parallel with each other, a plurality of sheet cutting stages for positioning the mother ceramic sheets drawn out from the plurality of reels respectively, a stacking jig for stacking ceramic sheets obtained by punching a region including at least one of the electrode patterns from one of the mother ceramic sheets thereon, an optical sensor for detecting positions of the registration marks of the mother ceramic sheets provided on the sheet cutting stages, and a cutting head, being movable between the plurality of sheet cutting stages and the stacking jig and having a periphery enclosed with a cutting edge for punching the regions of the mother ceramic sheets including the electrode patterns, which is adapted to carry ceramic sheets punched out from the mother ceramic sheets.

According to the present invention, the mother ceramic sheets provided with the electrode patterns are first taken up on the reels. Thus, it is possible to store the mother ceramic sheets with the electrode patterns wound on the reels, and the step of forming the electrode patterns by printing etc. can be separated from the later sheet cutting and stacking steps.

In the sheet cutting and stacking steps, a plurality of types of reels are set to punch out an arbitrary number of ceramic sheets from an arbitrary one of the mother ceramic sheets wound on the reels in accordance with a prescribed program, and then the ceramic sheets are stacked with each other.

In the sheet cutting step, the positions where the mother ceramic sheets are to be punched are corrected on the basis of the registration marks, which are simultaneously printed with the electrode patterns in constant positional relations thereto, in order to cut the ceramic sheets.

After the mother ceramic sheet is punched by the cutting head, the ceramic sheets are directly carried by the cutting head and stacked with each other on the stacking jig.

According to the present invention, the mother ceramic sheets provided with the electrode patterns are first taken up on the reels so that the same can be separated from the later sheet cutting and stacking steps. Thus, it is possible to prepare the mother ceramic sheets provided with the electrode patterns in a mass even for multi-item dab production, thereby improving the material yield.

Since the mother ceramic sheets are stored wound on the reels, the ceramic sheets can be easily handled, thereby reducing the time required for exchanging the mother ceramic sheets in order to switch the items, etc.

Further, it is possible to stack ceramic sheets having different types of electrode patterns with each other in arbitrary order by setting a plurality of reels wound with a respective plurality of types of mother ceramic sheets. In addition, it is possible to set reels and mother ceramic sheets to be used in manufacturing a subsequent product lot on nonused reel stand and sheet cutting stages, so that the setup time can be reduced to advantageously cope with multi-item dab production.

Since the ceramic sheets are punched out on the basis of the registration marks, which are formed with constant positional relations to the electrode patterns, and then stacked with each other, it is possible to stack ceramic sheets of a type generating static electricity therebetween or ceramic sheets having extremely small thicknesses, unlike with to the conventional system of aligning the ceramic sheets with each other on the basis of their end surfaces. When the electrode patterns and the registration marks are simultaneously formed by printing, print patterns therefor may simply be adjusted so that the registration marks come into the visual field of an optical sensor such as a CCD camera. Thus, the time for exchanging the print patterns is reduced.

The ceramic sheets are punched out from the mother ceramic sheet by the cutting head on the basis of the registration marks, directly carried by the cutting head onto the stacking jig, and stacked with each other on the stacking jig. Therefore, it is possible to prevent errors which may be caused before the cut ceramic sheets are inserted in the stacking jig.

Thus, the ceramic sheets can be stacked with each other with high accuracy, to enable manufacturing of a high capacity multilayer ceramic capacitor, for example.

If defects are caused in the electrode patterns by errors in printing, the mother ceramic sheets may simply be moved to skip such defective patterns, in order to readily cope with such errors.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
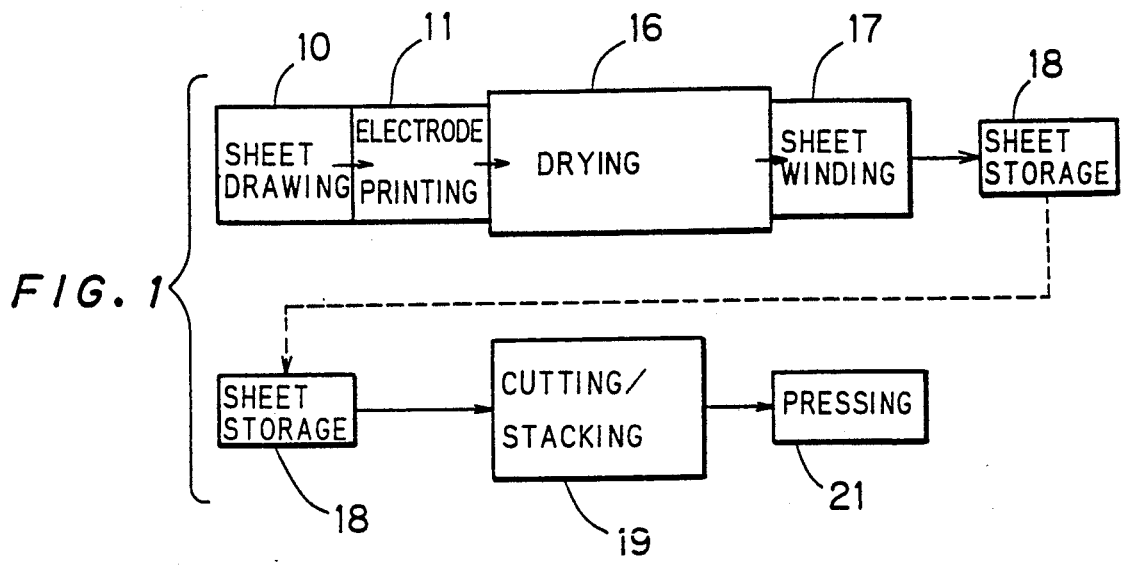
FIG. 1 is a block diagram showing an exemplary production line for manufacturing a ceramic layered product, including an embodiment of the present invention.

FIG. 1 schematically illustrates an exemplary production line for manufacturing a multilayer ceramic capacitor, which employs an embodiment of the method of the present invention.

Referring to FIG. 1, a long mother ceramic sheet, which is prepared by any well-known method, is set in a sheet drawing station 10, and drawn out therefrom toward an electrode printing station 11. The mother ceramic sheet may be prepared from a ceramic green sheet which is backed by an appropriate reinforcing sheet, or from an independent ceramic green sheet.

Figure 2:
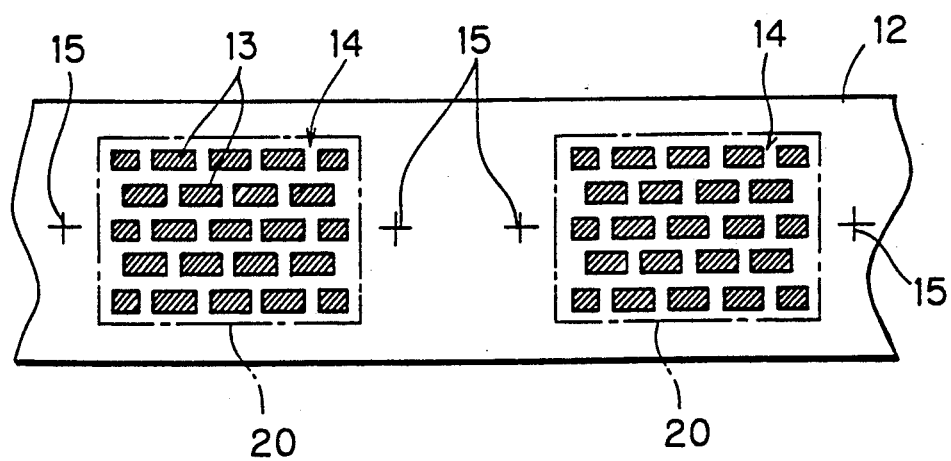
FIG. 2 is a plan view showing a part of a mother ceramic sheet 12.

In the electrode printing station 11, a plurality of electrode patterns 14, each including a plurality of electrodes 13, are printed on the mother ceramic sheet 12 as shown in FIG. 2. The plurality of electrode patterns 14 are distributed along the longitudinal direction of the mother ceramic sheet 12. Simultaneously with such printing of the electrode patterns 14, registration marks 15 having constant positional relations to the electrode patterns 14 are printed on the mother ceramic sheet 12.

The electrode patterns 14 and the registration marks 15 printed in the aforementioned manner are thereafter dried in a drying station 16.

Then, the mother ceramic sheet is wound on a reel in a sheet winding station 17.

In such a manner, a plurality of reels, which are wound with a respective plurality of types of mother ceramic sheets, are prepared as needed. The reels wound with the mother ceramic sheets are stored in a sheet storage station 18.

Then, the reels containing desired types of mother ceramic sheets are selected from the plurality of reels which are stored in the sheet storage station 18, and set in a cutting/stacking station 19. In the cutting/stacking station 19, regions 20 including the electrode patterns 14 are punched from each mother ceramic sheet 12 as shown in FIG. 2, and then the ceramic sheets punched out from the mother ceramic sheet 12 are stacked with each other.

A ceramic layered product, which is formed by the stacked ceramic sheets, is then pressed in a pressing station 21.

The cutting/stacking station 19 will now be described in detail with reference to FIGS. 3 to 9.

Figure 3:
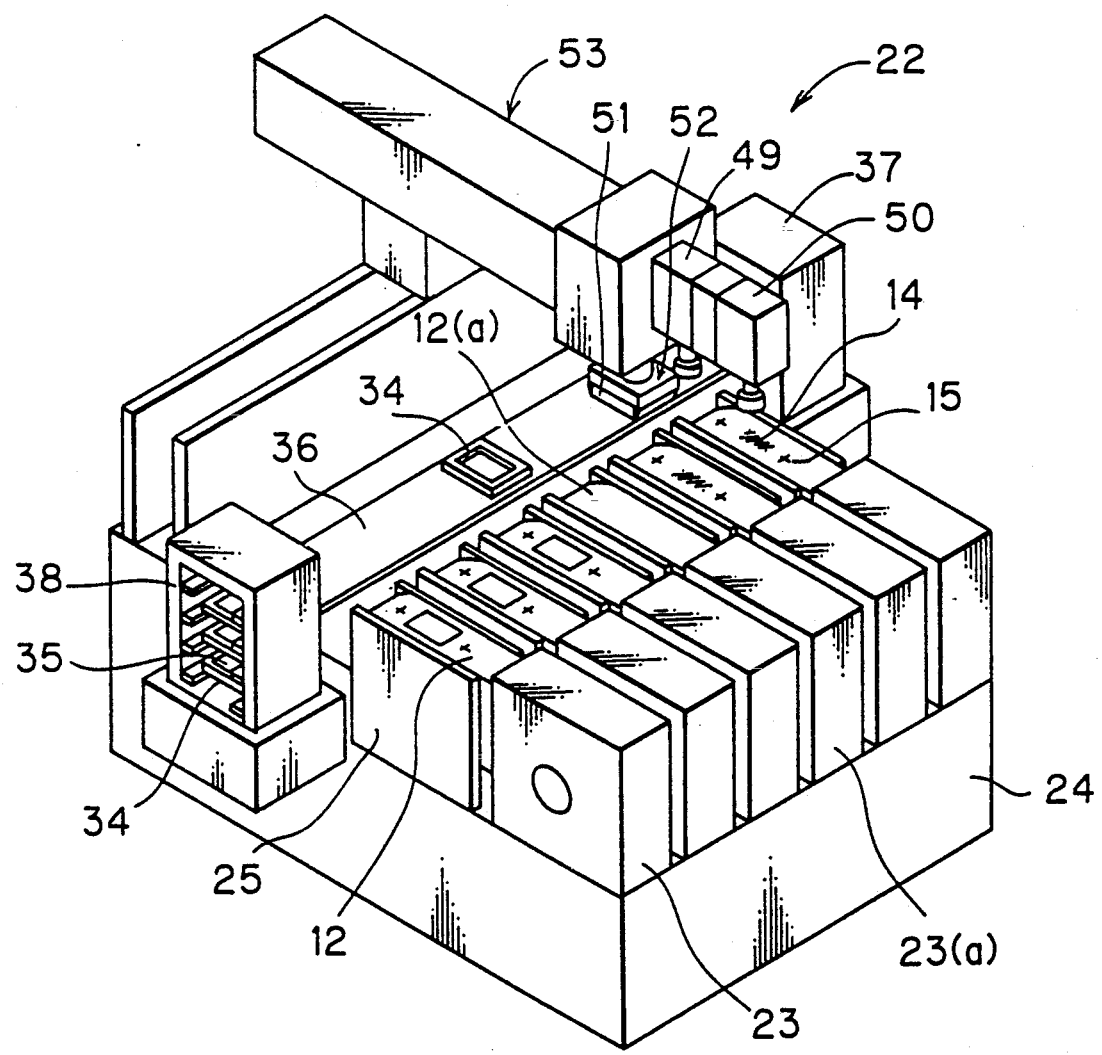
FIG. 3 is a perspective view showing a cutting/stacking device 22.

FIG. 3 is a perspective view showing the overall structure of a cutting/stacking device 22 which is employed in the cutting/stacking station 19.

The cutting/stacking device 22 comprises a reel stand 24 for setting six reels 23, for example, which are selected from the plurality of reels containing different types of mother ceramic sheets stored in the sheet storage station 18 shown in FIG. 1, oriented parallel with each other. While FIG. 3 illustrates the reels 23 as containers in the form of equilateral square poles, the reels are rotatably stored within such containers in practice, so that the mother ceramic sheets 12 are drawn out from openings provided in parts of the containers.

Figure 4:
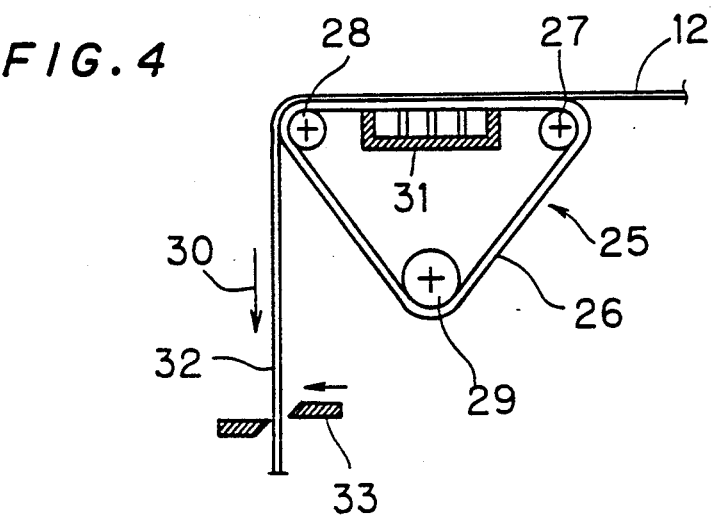
FIG. 4 is a sectional view showing a structure employed for a sheet cutting stage 25.

The mother ceramic sheets 12 drawn out from the reels 23 are positioned on sheet cutting stages 25 respectively. FIG. 4 shows the structure of each sheet cutting stage 25.

Referring to FIG. 4, each sheet cutting stage 25 includes a belt conveyor mechanism which is formed by a mesh belt 26. The mesh belt 26 is extended along three rollers 27, 28 and is 29, and driven to move the mother ceramic sheet 12 along the arrow 30. When the mother ceramic sheet 12 is on a horizontally directed path, a suction device 31 attracts the mother ceramic sheet 12 through the mesh belt 26, thereby positioning the sheet. This sheet cutting stage 25 is adapted to punch the regions 20 (FIG. 2) of the mother ceramic sheet 12 including the electrode patterns 14 as hereinafter described in detail. A resulting scrap sheet 32 is cut into pieces by a cutter 33 every feed.

Figure 5:
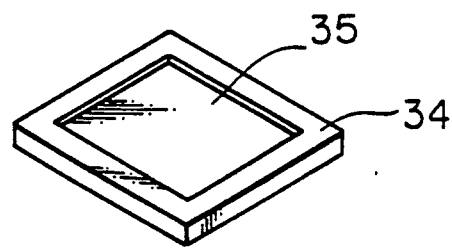
FIG. 5 is a perspective view showing a stacking jig 34.

Referring again to FIG. 3, stacking jigs 34 are arranged in the vicinity of the sheet cutting stages 25. FIG. 5 is an enlarged view showing a stacking jig 34, which is adapted to stack a prescribed number of ceramic sheets 35 obtained by punching out the regions 20 including the electrode patterns 14 from the mother ceramic sheet 12. The stacking jig 34 comprises a bottom wall, and a frame for peripherally enclosing the ceramic sheets 35 which are stacked on the bottom wall.

Figure 6:
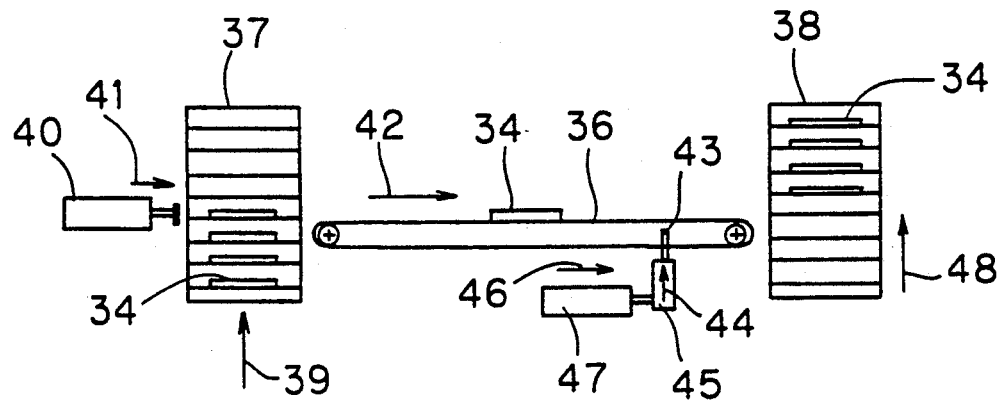
FIG. 6 is a front elevational view illustrating a conveyor 36 and a structure related thereto.

As shown in FIG. 3, the stacking jigs 34 are placed on a conveyor 36. A loading rack 37 is arranged on the upstream side of the conveyor 36 in order to supply the stacking jigs 34 to the conveyor 36, while an unloading rack 38 is arranged on the downstream side of the conveyor 36 in order to take the stacking jigs 34 out of the conveyor 36. FIG. 6 also shows the conveyor 36, the loading rack 37 and the unloading rack 38.

Referring to FIGS. 3 and 6, a plurality of vacant stacking jigs 34 holding no ceramic sheets are placed on respective stages on the loading rack 37. As shown by the arrow 39, the respective stages of the loading rack 37 are displaced to be successively aligned with the upper surface of the conveyor 36. When a prescribed stage is aligned with the upper surface of the conveyor 36, a piston of a cylinder 40 is driven along the arrow 41 to eject the vacant stacking jig 34 onto the conveyor 36. The stacking jig 34 thus placed on the conveyor 36 is carried by the conveyor 36 along the arrow 42, and carried toward a prescribed position on the conveyor 36. At this prescribed position, the ceramic sheets 35 are stacked on the stacking jig 34 as shown in FIG. 5.

After the ceramic sheets 35 are stacked on the stacking jig 34, the conveyor 36 is driven along the arrow 42, to carry the stacking jig 34 to a position immediately ahead of the unloading rack 38. At this position, a vertical cylinder 45 is driven to move a push-in pawl 43 along the arrow 44 while a horizontal cylinder 47 is driven to move the vertical cylinder 45 along the arrow 46. Thus, the stacking jig 34 is pushed onto a prescribed stage of the unloading rack 38. As shown by the arrow 48, the respective stages of the unloading rack 38 are displaced to be successively aligned with the upper surface of the conveyor 36. Thus, the unloading rack 38 is adapted to store a plurality of stacking jigs 34 that have received the stacked ceramic sheets 35. After the unloading rack 38 is filled up with the stacking jigs 34, it is detached from the cutting/stacking device 22, so that the stacking jigs 34 are carried to a next step, i.e., the pressing station 21 shown in FIG. 1, with the unloading rack 38.

Referring to FIG. 3, CCD cameras 49 and 50 are arranged above the sheet cutting stages 25, in order to detect the positions of the registration marks 15 which are provided on the mother ceramic sheet 12. In order to punch the regions 20 (FIG. 2) of the mother ceramic sheets 12 including the electrode patterns 14, a cutting head 52, whose periphery is enclosed with a cutting edge 51, is arranged in the vicinity of the CCD cameras 49 and 50.

According to this embodiment, the cutting head 52 and the CCD cameras 49 and 50 are mounted on an $XY\theta$ robot 53, so that the same are movable in directions X, Y and $\theta$. The cutting head 52 and the CCD cameras 49 and 50 may alternatively be driven by separate driving systems.

Figure 7:
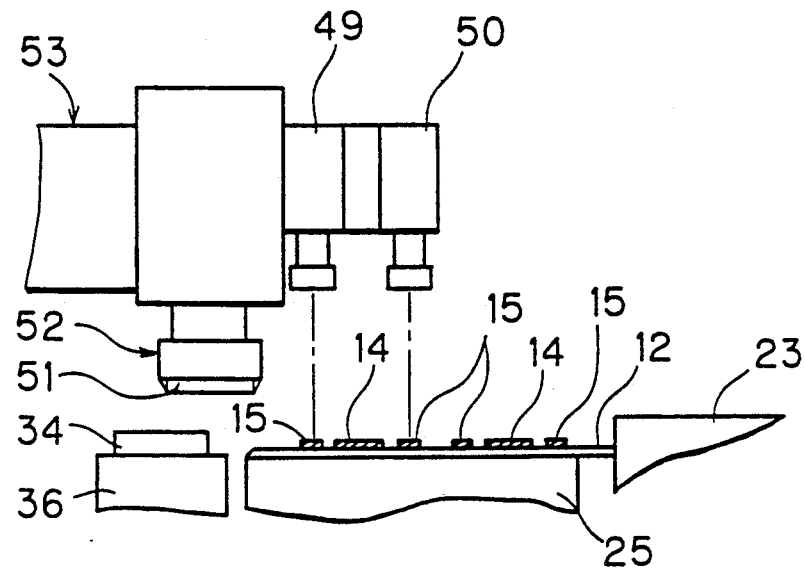
FIGS. 7, 8 and 9 are front elevational views for illustrating operations of a cutting head 52 and CCD cameras 49 and 50.
Figure 8:
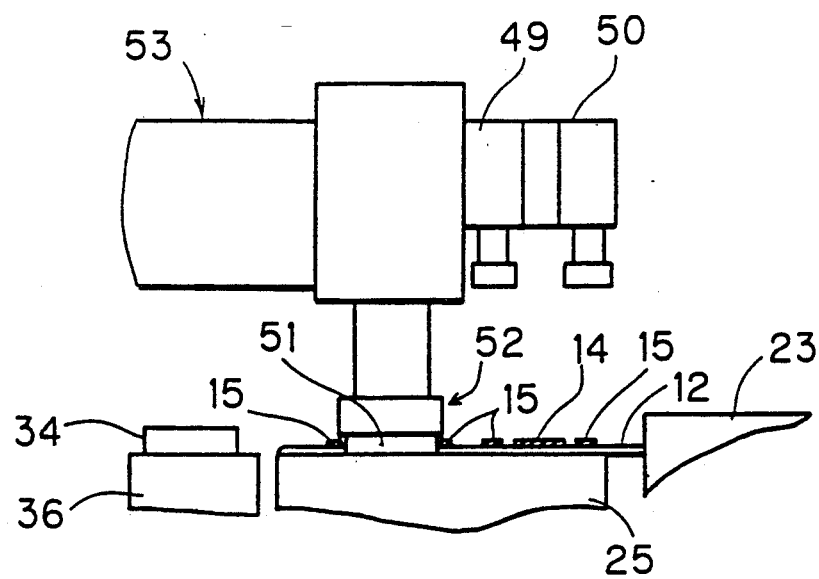
Figure 9:
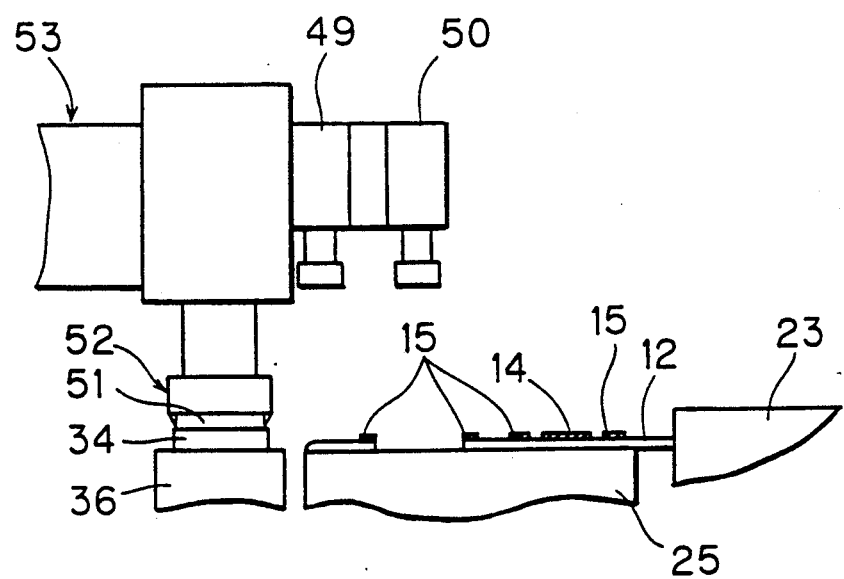
Figure 10:
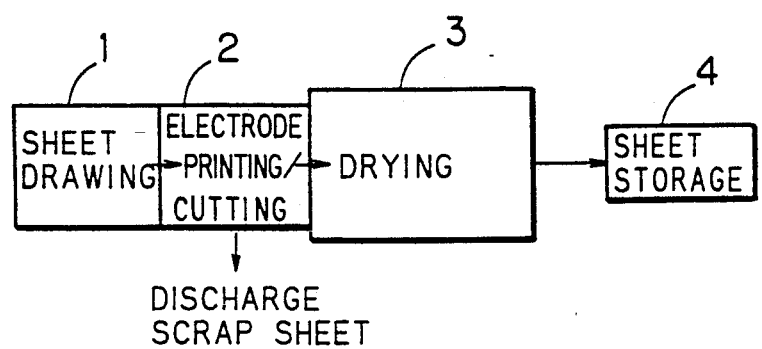
FIG. 10 is a block diagram showing a conventional production line for manufacturing a ceramic layered product, which is of interest to the present invention.
Figure 11:
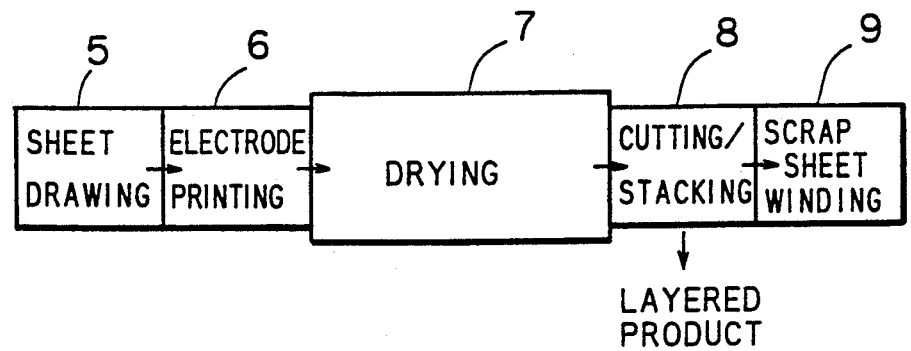
FIG. 11 is a block diagram showing a production line for manufacturing a ceramic layered product, proposed by the applicant, which is not yet known in the art.

FIGS. 7, 8 and 9 show the operations of the cutting head 52 and the CCD cameras 49 and 50.

As shown in FIG. 3, the mother ceramic sheets 12 are drawn out from the plurality of reels 23 onto related sheet cutting stages 25 and fixed thereto respectively. As hereinabove described, this operation is achieved by the structure shown in FIG. 4. FIG. 7 shows another view of the process at this stage.

As seen in FIG. 7, a prescribed one is selected from the plurality of mother ceramic sheets 12, and the XYθ robot 53 is so driven that the registration marks 15 provided on the selected mother ceramic sheet 12 come into the visual fields of the CCD cameras 49 and 50. The CCD cameras 49 and 50 image-process the positions of the registration marks 15. The results of such image processing are applied to a computer (not shown), which in turn calculates corrected values as to the positions where the mother ceramic sheet 12 should be punched.

Then, as shown in FIG. 8, the XYθ robot 53 is driven in response to the aforementioned corrected values, to move the cutting head 52 toward the mother ceramic sheet 12. Thus, the regions 20 provided with the electrode patterns 14 as shown in FIG. 2 are punched. The punched ceramic sheets, which are hidden by the cutting edge 51 and not shown in FIG. 8, are carried away from the cutting position by the cutting head 52. In order to carry the punched ceramic sheets reliably, the cutting head 52 comprises a vacuum function device (not shown) for holding the punched ceramic sheets by suction.

As shown in FIG. 9, the cutting head 52 is driven by the XYθ robot 53 to carry the ceramic sheets to the stacking jig 34 which is placed on the conveyor 36, and stacks the ceramic sheets one upon the other on the stacking jig 34.

The aforementioned operations are repeated so that any arbitrary member of ceramic sheets are stacked on the stacking jig 34 in arbitrary order.

In order to obtain a ceramic layered product for manufacturing a multilayer ceramic capacitor, it is necessary to also stack ceramic sheets which are provided with no electrode patterns. Therefore, preferably at least one of the reels 23 set on the reel stand 24, i.e., a mother ceramic sheet 12(a) which is drawn out from a reel 23(a), is provided with no electrode patterns, etc., as shown in FIG. 3. In this case, the mother ceramic sheet 12(a) may simply be drawn out at a constant amount since it is not necessary to correctly position any electrode pattern on the mother ceramic sheet 12(a) before punching.

As hereinabove described, the prescribed ceramic sheets 35 which are stacked on the stacking jig 34 are subjected to hydrostatic pressing, for example, in the pressing station 21 shown in FIG. 1, and thereafter cut to obtain single chips for multilayer ceramic capacitors. Then each chip is fired and provided with external electrodes, to obtain a desired multilayer ceramic capacitor.

In the aforementioned embodiment, the reels 23 are stored in containers, so that the mother ceramic sheets 12 can be easily stored so as to remain clean. However, if such an advantage is not desired, it is not necessary to store the reels in containers.

The present invention is not restricted to manufacturing a ceramic layered product for a multilayer ceramic capacitor, but is also applicable to manufacturing layered products for other types of multilayer ceramic electronic components such as a multilayer inductor, a multilayer LC filter, a multilayer circuit board, or the like.

Although the present invention has been described and illustrated in detail, it is clearly understood that the same is by way of illustration and example only and is not to be taken by way of limitation, the scope of the present invention being limited only by the terms of the appended claims.

What is claimed is:

1. A method of manufacturing a ceramic lamina comprising the steps of:
   a) preparing a plurality of reels wound with a respective plurality of elongated mother ceramic sheets, each having a plurality of electrode patterns, and a plurality of registration marks, said registration marks having predetermined relative locations on said sheets with respect to said electrode patterns, distributed along its longitudinal direction;
   b) drawing out said mother ceramic sheets from respective ones of said plurality of reels onto corresponding sheet cutting stages;
   c) determining the location of a region including at least one of said electrode patterns within one of said mother ceramic sheets on a selected said sheet cutting stage, on the basis of said registration marks, and punching out a first ceramic sheet corresponding to said region from said mother ceramic sheet employing a cutting head whose periphery is enclosed with a cutting edge; and
   d) carrying said first ceramic sheet punched out of said mother ceramic sheet to a stacking jig employing said cutting head and stacking said first ceramic sheet on said stacking jig.

2. A method of manufacturing a ceramic lamina in accordance with claim 1, wherein said step of preparing a plurality of reels comprises the step of storing a plurality of reels and the step of selecting said ones of said stored plurality of reels from which said mother ceramic sheets are drawn out.

3. A method of manufacturing a ceramic lamina in accordance with claim 2, wherein said step of storing said plurality of reels comprises the step of storing said reels in containers.

4. A method of manufacturing a ceramic lamina in accordance with claim 1, wherein said mother ceramic sheets are intermittently drawn out in said step of drawing out said mother ceramic sheets from said reels, and said step of punching said one of said mother ceramic sheets employing said cutting head is carried out when said mother ceramic sheet is in a stopped state.

5. A method of manufacturing a ceramic lamina in accordance with claim 4, further comprising the step of cutting a scrap sheet resulting from said step of punching said one of said mother ceramic sheets employing said cutting head, for every intermittent step of drawing out said mother ceramic sheet.

6. A method of manufacturing a ceramic lamina in accordance with claim 1, further comprising the steps of:
   e) repeating said step (c) to punch out a second said ceramic sheet; and
   f) carrying said second ceramic sheet to said stacking jig and stacking said second ceramic sheet on said first ceramic sheet.

7. A method of manufacturing a ceramic lamina in accordance with claim 6, further comprising the step of repeating said steps (a) and (f).

8. A method of manufacturing a ceramic lamina in accordance with claim 6, wherein said first and second ceramic sheets are punched from one said mother ceramic sheet.

9. A method of manufacturing a ceramic lamina in accordance with claim 6, wherein said first and second ceramic sheets are punched from different ones of said mother ceramic sheets.

11. A method of manufacturing a ceramic lamina in accordance with claim 9, further comprising the step of aligning said stacking jig with said respective different mother ceramic sheets during said steps (d) and (f).

11. A method of manufacturing a ceramic lamina in accordance with claim 1, further comprising the steps of:

preparing an insulation reel wound with a respective elongated mother ceramic insulation sheet having no electrode pattern thereon;

drawing out said mother ceramic insulation sheet from said insulation reel onto a corresponding sheet cutting stage;

punching out an insulation ceramic sheet from said mother insulation ceramic sheet; and carrying said insulation ceramic sheet to said stacking jig and stacking it on said first ceramic sheet.

* * * * *